(12) United States Patent
Suyama et al.

(10) Patent No.: US 7,232,434 B2
(45) Date of Patent: Jun. 19, 2007

(54) CATHETER

(75) Inventors: Makoto Suyama, Kuroishi (JP); Tsutomu Nakamura, Hirosaki (JP)

(73) Assignee: Olympus Corporation, Tokyo (JP)

( * ) Notice: Subject to any disclaimer, the term of this patent is extended or adjusted under 35 U.S.C. 154(b) by 249 days.

(21) Appl. No.: 10/095,824

(22) Filed: Mar. 14, 2002

(65) Prior Publication Data
US 2004/0077929 A1    Apr. 22, 2004

(30) Foreign Application Priority Data
Mar. 16, 2001 (JP) .............................. 2001-076166

(51) Int. Cl.
 *A61M 25/00* (2006.01)
(52) U.S. Cl. ..................... 604/528; 600/139
(58) Field of Classification Search ................ 604/510, 604/95.01, 94.04, 164.13, 528; 600/434, 600/585, 114, 146, 139, 149
See application file for complete search history.

(56) References Cited

U.S. PATENT DOCUMENTS

| | | | | |
|---|---|---|---|---|
| 4,911,148 A | * | 3/1990 | Sosnowski et al. | 600/136 |
| 5,238,005 A | * | 8/1993 | Imran | 600/585 |
| 5,325,845 A | * | 7/1994 | Adair | 600/114 |
| 5,378,234 A | * | 1/1995 | Hammerslag et al. | 604/95.04 |
| 5,381,782 A | * | 1/1995 | DeLaRama et al. | 600/149 |
| 5,603,697 A | * | 2/1997 | Grundy et al. | 604/95.04 |
| 6,102,886 A | * | 8/2000 | Lundquist et al. | 604/22 |
| 6,126,633 A | * | 10/2000 | Kaji et al. | 604/95.04 |
| 6,146,338 A | * | 11/2000 | Gardeski et al. | 600/585 |

FOREIGN PATENT DOCUMENTS

| | | |
|---|---|---|
| DE | 38 29 603 A1 | 3/1990 |
| DE | 690 29 358 T2 | 4/1991 |
| DE | 692 29 147 T2 | 1/1993 |
| DE | 199 24 440 A1 | 12/2000 |
| JP | 5-38342 | 2/1993 |

* cited by examiner

*Primary Examiner*—Nicholas D. Lucchesi
*Assistant Examiner*—Christopher D. Koharski
(74) *Attorney, Agent, or Firm*—Scully, Scott, Murphy & Presser, P.C.

(57) ABSTRACT

A catheter according to an aspect of the present invention comprises a flexible tubular insert section having, in the outer surface of the distal end side of the insert section, a plurality of notches arranged in the longitudinal direction of the insert section on one side of a plane passing through the longitudinal axis of the insert section, an operating wire passed through the insert section and capable of advancing or retreating to bend the distal end side of the insert section having the notches, and a reinforcing tube put on the insert section to cover substantially the overall length of the whole region of the insert section, except the distal end side of the insert section on which the notches are formed, and to restrain longitudinal compression of the insert section.

20 Claims, 6 Drawing Sheets

CATHETER

CROSS REFERENCE

The present disclosure relates to subject matter contained in Japan Patent Application No. 2001-76166 filed on Mar. 16, 2001 which is expressly incorporated herein by reference in its entireties.

BACKGROUND OF THE INVENTION

The present invention relates to a catheter adapted to be inserted into a narrow region, such as a duct of a living body, and used to perform medical operations, such as injection of a contrast medium, recovery of foreign substances, extraction of cells, ablation of affected parts, insertion of a guide wire, etc.

A catheter that is inserted into a duct of a living body or the like, in order to perform medical operations, such as injection of a contrast medium, recovery of foreign substances, extraction of cells, ablation of affected parts, insertion of a guide wire, etc., generally comprises a flexible elongate insert section and an operating section on the hand side. The distal end side of the insert section can be bent so that the distal end of the insert section is directed toward a desired region in the living body. More specifically, the distal end side of the insert section can be bent by pushing or pulling an operating wire, which is fixedly connected to the distal end portion of the insert section, by means of the operating section on the hand side.

Operation for guiding the catheter into a narrow region deep in the living body is very difficult and requires considerable skill. FIG. 12 shows the way a catheter 102 is guided through the channel of an endoscope 100 to a region near a duodenal papilla 105, and an operative instrument 104 is inserted into a bile duct 106 through the opening of the duodenal papilla 105 by means of the catheter 102 that projects from the channel of the endoscope 100. In this operation, the operative instrument 104 that is inserted in a lumen of the catheter 102, cannot be inserted through the duodenal papilla 105 into the bile duct 106 unless the distal end side of an insert section 102a of the catheter 102 is bent to a given degree in a given direction such that the distal end of the insert section 102a can be exactly directed toward the opening of the duodenal papilla 105.

Conventionally, various attempts have been made to direct the distal end of a catheter toward a desired region of a living body. Described in Jpn. Pat. Appln. KOKAI Publication No. 5-38342, for example, is a technique in which the distal end side of the insert section 102a of the catheter 102 is provided with a plurality of notches 103 that are eccentric to the axis of the insert section 102a so that it easily bends to the side on which the notches 103 are located, as shown in FIG. 12, whereby the insert section 102 can be readily directed toward the target region.

If the insert section 102a is provided with the notches 103 that are eccentric to its axis, as described in Jpn. Pat. Appln. KOKAI Publication No. 5-38342, the bending direction of the insert section 102a can no doubt be regulated to some degree. However, this alone cannot be said to be a radical solution.

In order to guide the catheter 102 to the duodenal papilla 105, the flexible elongate insert section 102a of the catheter 102 is first inserted into the channel of the winding insert section of the endoscope 100 in the living body, and the distal end side of the insert section 102a is caused to project from the distal end of the insert section of the endoscope 100. Thereafter, the projected distal end side of the insert section 102a is bent and directed toward the duodenal papilla. The key factor in this operation is to protrude the insert section 102a of the catheter 102 from the distal end of the insert section of the endoscope 100 with that side of the insert section 102a for the notches 103 directed toward the duodenal papilla 105 (upper side of the drawing), and thereafter, the distal end side of the insert section 102a is bent to a desired degree without failing to maintain this direction of protrusion.

However, the insert section 102a of the catheter 102 may be inserted in any direction into the channel of the endoscope 100. Thus, if the catheter 102 is oriented when the catheter 102 starts to be inserted into the channel of the endoscope 100, the catheter 102 may be redirected by its own rotation or the like in the channel of the endoscope 100 as the catheter 102 passes through the channel of the endoscope 100 that winds intricately in the living body. Consequently, the catheter 102 may fail to be caused to project from the endoscope 100 with that side of the insert section 102a for the notches 103 directed toward the duodenal papilla 105, in some cases.

Even in the case where the catheter 102 can be caused to project from the endoscope 100 with that side for the notches 103 directed toward the duodenal papilla 105, moreover, the distal end of the catheter 102 cannot be directed successfully toward the duodenal papilla 105 unless the catheter 102 is bent without changing the direction of its projection. If the distal end portion of the catheter 102 is provided with the notches 103, in particular, the stiffness of the region with the notches 103 lowers, making it hard to steadily maintain the direction of projection of the catheter 102.

Since the catheter is elongate and flexible, the catheter inevitably meanders as the distal end side of the insert section of the catheter 102 is bent by pushing or pulling the operating wire. In some cases, therefore, a stroke on the hand side cannot be transmitted successfully to the distal end side, meaning that a desired curvature cannot be obtained. If the distal end side of the insert section 102a cannot be bent to a necessary degree, the distal end of the catheter 102 cannot be directed successfully toward the duodenal papilla 105.

Thus, if the catheter 102 cannot be caused to project from the endoscope with the specially provided notches 103 directed toward the duodenal papilla 105, it is hard to direct the distal end of the catheter 102 toward the duodenal papilla 105, in consequence. If the catheter 102 can be caused to project from the endoscope 100 with the notches 103 directed toward the duodenal papilla 105, moreover, the distal end side of the catheter 102 cannot be bent to a desired degree in a desired direction unless a handling force on the hand side can be efficiently accurately transmitted to the distal end side without failing to maintain the direction of its projection. Thus, the distal end of the insert section 102a cannot be directed toward the duodenal papilla 105 exactly and speedily.

BRIEF SUMMARY OF THE INVENTION

Objects of the present invention are to provide catheters that can fulfill at least one of functions (1) to cause an insert section to project in a desired direction from the distal end of an endoscope, (2) to maintain the direction of projection steadily, and (3) to transmit a handling force on the hand side efficiently and accurately to the distal end side, thereby directing the distal end of the insert section toward a desired region of a living body exactly and speedily.

At least one of the above objects is achieved by a catheter described below. More specifically, a catheter according to an aspect of the present invention comprises: a flexible tubular insert section formed having, in the outer surface of the distal end side of the insert section, a plurality of notches arranged in the longitudinal direction of the insert section on one side of a plane passing through the longitudinal central axis of the insert section; an operating wire passed through the insert section and capable of advancing and retreating to bend the distal end side of the insert section having the notches; a reinforcing tube put on the insert section to cover substantially the overall length of the whole region of the insert section except the distal end side of the insert section on which the notches are formed, and to restrain longitudinal compression of the insert section. Preferably, at least two reinforcing wires defining one plane substantially parallel to the longitudinal axis of the insert section are arranged in the longitudinal direction of the insert section on the one side of the insert section on which the notches are formed.

DETAILED DESCRIPTION OF THE INVENTION

Figure 1:
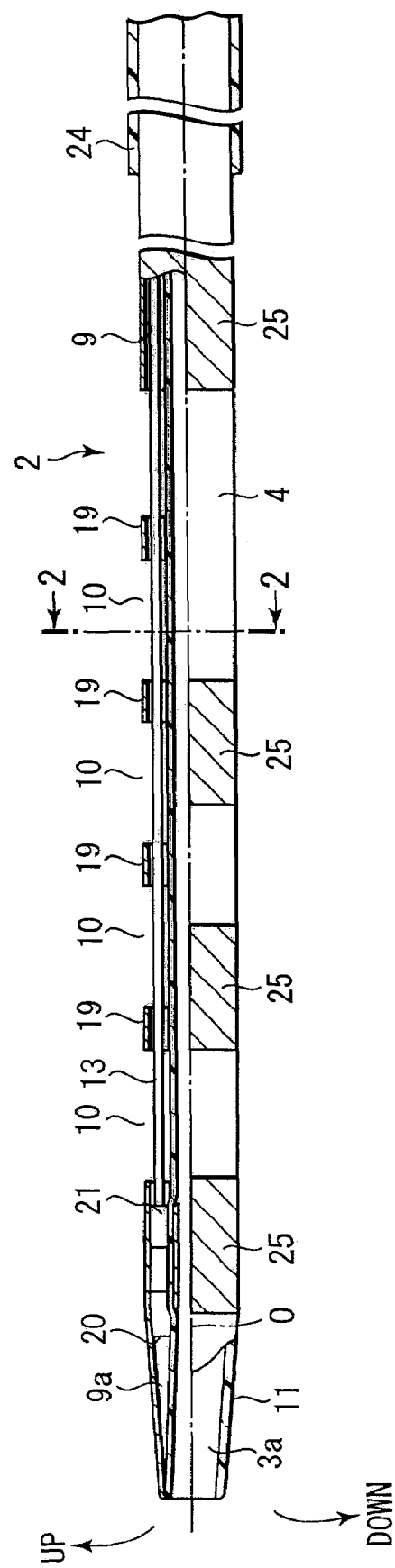
FIG. 1 is a schematic sectional view of an insert section of a catheter according to one embodiment of the present invention.
Figure 2:
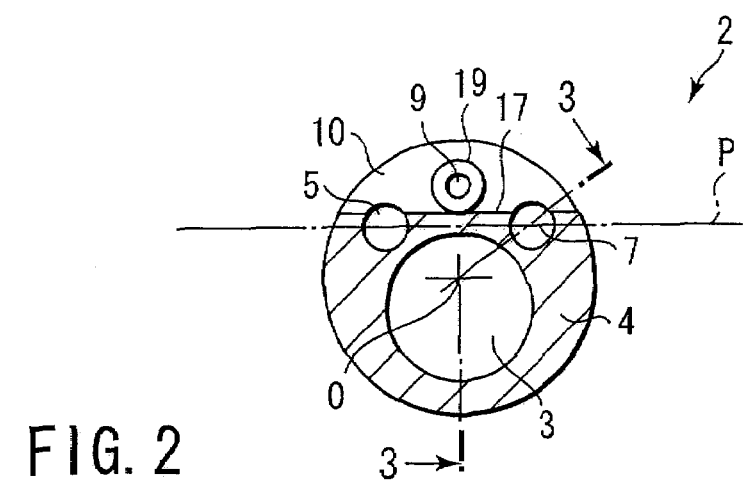
FIG. 2 is a sectional view taken along line 2—2 of FIG. 1.

One embodiment of the present invention will now be described with reference to the drawings.

FIGS. 1 to 4 show an insert section 2 of a catheter according to the one embodiment of the present invention. As shown in the drawings, the insert section 2 is formed of a flexible tube (flexible sheath) 4 having an elongate soft multi-lumen structure. As is definitely shown in FIG. 2, the tube 4 is formed having a large-diameter first lumen (liquid feed passage) 3 and small-diameter second to fourth lumens 5, 7 and 9, which extend throughout its length in the longitudinal direction. The central axis of the first lumen 3 has a given eccentricity to a longitudinal central axis O of the tube 4 on one side, while the respective longitudinal central axes of the small-diameter second to fourth lumens 5, 7 and 9 have given eccentricities to the longitudinal central axis O of the tube 4 on the other side. More specifically, the respective longitudinal central axes of the second and third lumens 5 and 7 have eccentricities to the longitudinal central axis O of the tube 4 that are opposite to and substantially equal to the eccentricity of the longitudinal central axis of the first lumen 3. Further, the respective central axes of the lumens 5 and 7 are situated substantially symmetrically with respect to a plane that passes through the longitudinal central axis O of the tube 4 and the longitudinal central axis of the first lumen 3. Furthermore, the longitudinal central axis of the fourth lumen 9 is much more eccentric to the longitudinal central axis O of the tube 4 than those of the second and third lumens 5 and 7 are, and is situated between the second and third lumens 5 and 7.

As shown in FIG. 1, the outer surface of the tube 4 on the distal end side is formed having a plurality of notches (slits or portions that are lower in resistance to axial compression than the proximal end side of the tube 4 is) 10 on the opposite side of the longitudinal central axis O of the tube 4 to the first lumen 3 (i.e., on the side where the second to fourth lumens 5, 7 and 9 are formed). These notches 10 are formed by notching the tube 4 in a direction substantially perpendicular to its longitudinal central axis O, and are arranged at given spaces from one another in the longitudinal direction of the tube 4. The depth of the notches 10 is adjusted to a dimension such that they completely diametrically cross the fourth lumen 9 without reaching the first lumen 3. Thus, on the distal end side of the tube 4, these notches 10 define a plurality of tubular portions 19 that are spaced in the longitudinal direction from one another and intermittently form a part of the fourth lumen 9.

Figure 11A:
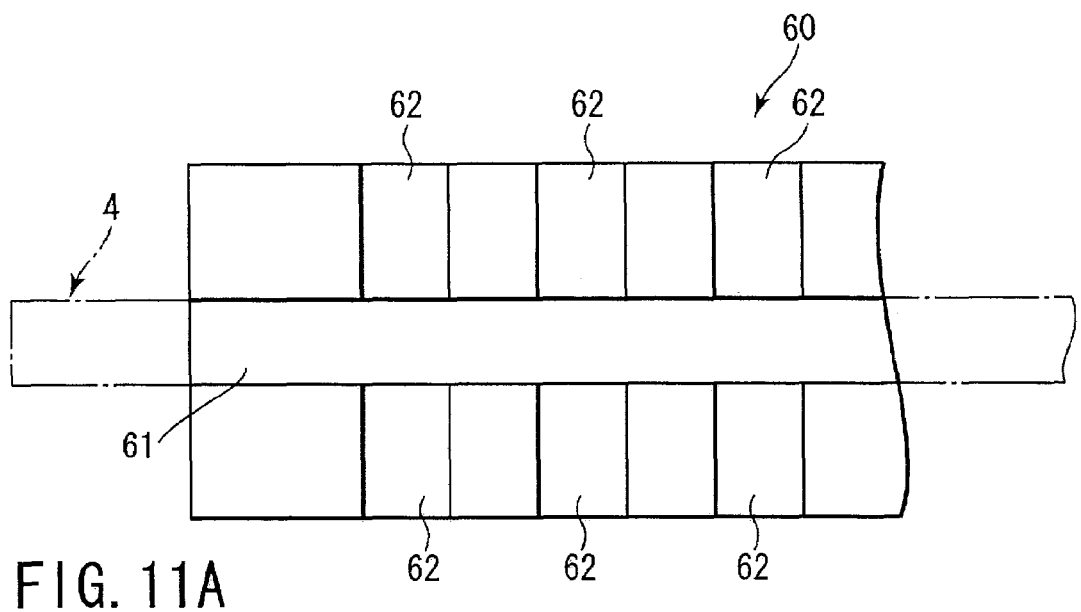
FIG. 11A is a plan view of a tool for forming notches.
Figure 11B:
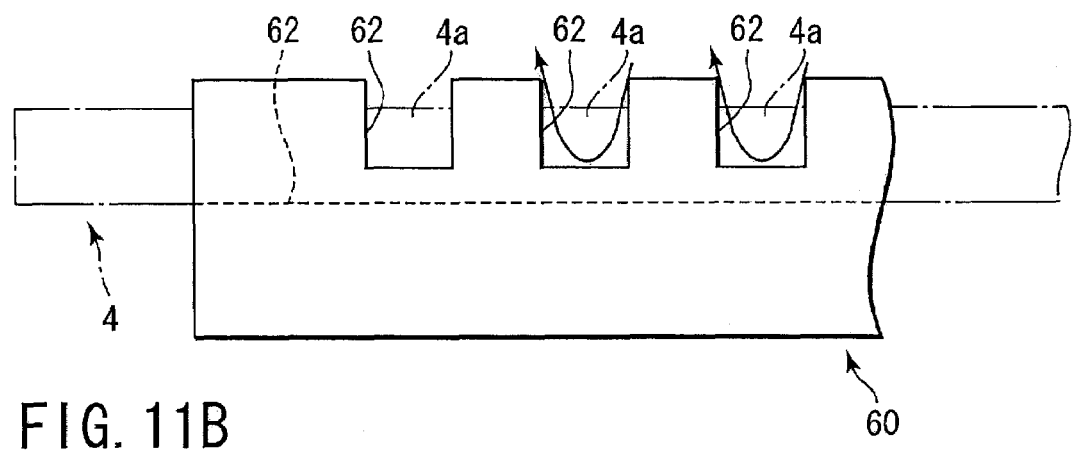
FIG. 11B is a side view of the tool of FIG. 11A.

FIGS. 11A and 11B show a tool for forming the notches 10 in the tube 4. As shown in the drawings, a tool 60 has a longitudinal groove 61 in which the tube 4 is placed and a plurality of cross grooves 62 that cross the groove 61 at right angles to it. The shape of the cross grooves 62 corresponding to the shape of the notches 10 to be formed in the tube 4. The width of the longitudinal groove 61 is substantially equal to the outside diameter of the tube 4. The respective depths of the longitudinal groove 61 and the cross grooves 62 are adjusted to dimensions such that the width and depth of the notches 10 to be formed in the tube 4 can be obtained when those regions 4a of the tube 4 which are exposed in the cross grooves 62, as the tool 60 is viewed sideways with the tube 4 located in the longitudinal groove 61, are cut, as shown in FIG. 11B. Thus, if the regions 4a of the tube 4 that are exposed in the cross grooves 62 as viewed sideways with the tube 4 located in the longitudinal groove 61 are cut along the shape of the cross grooves 62, as indicated by arrows in FIG. 11B, the notches 10 can be easily formed in a short time, and the working accuracy can be improved.

Figure 3:
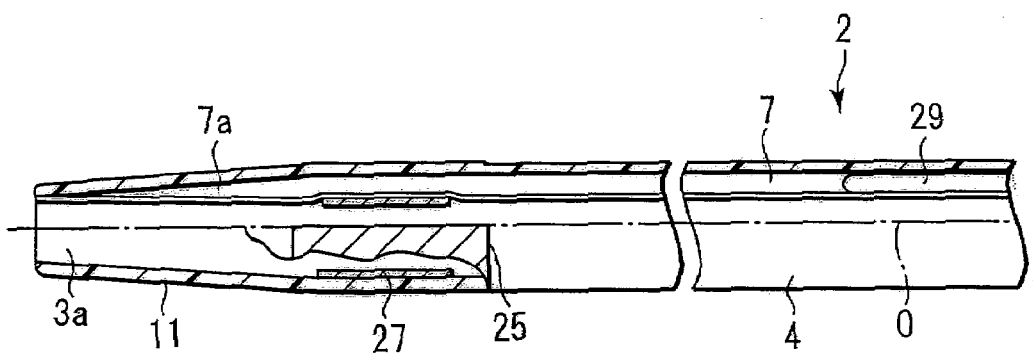
FIG. 3 is a sectional view taken along line 3—3 of FIG. 2.

As is clearly shown in FIGS. 1 and 3, a distal end portion 11 of the tube 4 is tapered, and corresponding to this, the respective distal end portions of the second to fourth lumens 5, 7 and 9 define taper holes 5a, 7a and 9a. The distal end portion of the first lumen 3 secures an inside diameter that allows injection of a desired quantity of contrast medium and insertion of a guide wire of a desired size, and forms an opening 3a (taper hole 5a is not shown).

An operating wire 13 for bending the distal end side of the tube 4 is movably passed through the fourth lumen 9. At least a part of the operating wire 13 is formed of a single wire. The distal end side of the operating wire 13 passes through the tubular portions 19, which are defined by the notches 10, and reaches the inside of the taper hole 9a. A part of the distal end side is exposed to the outside through the notches 10. In this case, the operating wire 13 is not situated beyond the outside diameter of the tube 4 at least on the distal end side of the tube 4 on which the notches 10 are formed. Further, an end tip 21 having tapered step portions is fixed to the distal end of the operating wire 13. The end tip 21 is composed of a plurality of cylindrical portions having a profile substantially in the shape of a frustum (or having the form of a bamboo shoot) and connected in the longitudinal direction. The end tip 21 and the operating wire 13 are fixed to each other in a manner such that the distal end of the operating wire 13 is plasma-welded to the distal end of the end tip 21 with the distal end portion of the operating wire 13 passed through the bore of the end tip 21.

The respective edge portions (corner portions) of the tapered step portions of the end tip 21 bite the inner surface of the tube 4 that forms the fourth lumen 9, or more specifically, the inner surface of the taper hole 9a, whereby the operating wire 13 is fixed to the distal end of the tube 4 by means of the end tip 21. Thus, if the operating wire 13 is pushed out toward the distal end side in the fourth lumen 9, the distal end side of the tube 4 bends in the DOWN direction shown in FIG. 1. If the operating wire 13 is pulled toward the hand side (proximal end side) in the fourth lumen 9, on the other hand, the distal end side of the tube 4 bends in the UP direction shown in FIG. 1. In order to reconfirm the fixation of the operating wire 13 to the tube 4, the operating wire 13 may be fixedly bonded to the tube 4 with an adhesive agent applied to, for example, the leading notch 10 through which the operating wire 13 is exposed.

Reinforcing wires (hereinafter referred to as stabilizers) 29 are passed through the second and third lumens 5 and 7, individually. The two stabilizers 29 define one plane P (see FIG. 2) that is parallel to the longitudinal central axis O of the tube 4 (also parallel to a base 17 of each notch 10 according to the present embodiment). This plane P determines the direction of the notches 10 when the tube 4 is introduced into a living body or a channel of an endoscope. Thus, the stabilizers 29 serve to stabilize the passing and bending operations for the tube 4 in the rotating direction. The respective proximal ends of the stabilizers 29 are fixed to an operating section 40 (mentioned later) of the catheter.

Further, a reinforcing tube 24 formed of a heat-shrinkable tube is put on the outer peripheral surface of the tube 4, substantially covering the overall length of the insert section 2 except the distal end side on which the notches 10 are formed. During the bending operation for the tube 4 by means of the operating wire 13, the reinforcing tube 24 restrains longitudinal compression of the tube 4, thereby preventing the tube 4 from meandering.

Figure 4:
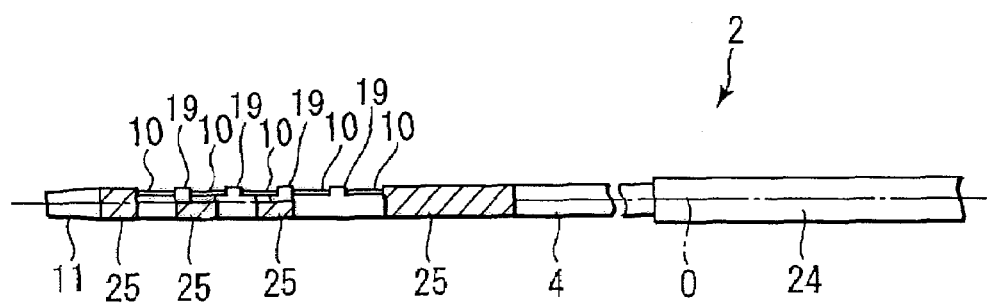
FIG. 4 is a side view of the insert section of FIG. 1.

As shown in FIGS. 1 and 4, moreover, the distal end portion of the tube 4 is provided with a plurality of markings 25 that are spaced in the longitudinal direction from one another. These markings 25 can show the depth of insertion of the tube 4 in a duodenal papilla. As shown in FIG. 3, moreover, the distal end of the tube 4 is provided with an X-ray-impermeable tip 27 that indicates the position of the distal end of the tube 4.

Figure 5:
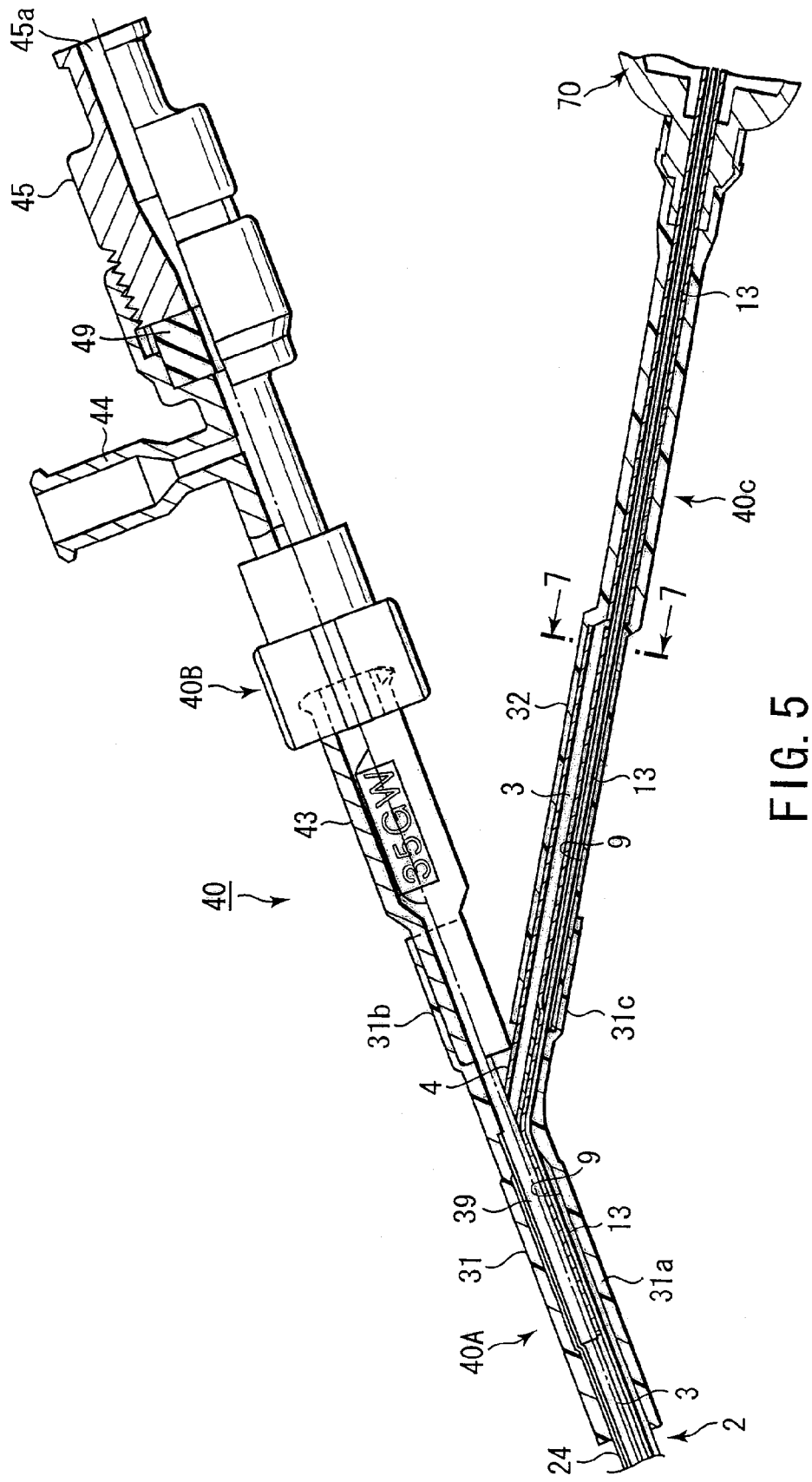
FIG. 5 is a sectional view of an operating section of the catheter according to the one embodiment of the present invention taken along line 5—5 of FIG. 7.

FIGS. 5 to 10 show the operating section (operator) 40 of the catheter according to the present invention. As shown in FIG. 5, the operating section 40 is composed of a connecting portion 40A, which is connected to the insert section 2, and an introducer 40B and an operator 40C that are separately connected to the proximal end of the connecting portion 40A. The introducer 40B is formed of a tubular body 43, and is used to introduce the contrast medium, guide wire, etc. Further, the operator 40C is formed of connecting pipe portion 32 and an operator body 70, and is used to advance and retreat the operating wire 13.

Figure 6:
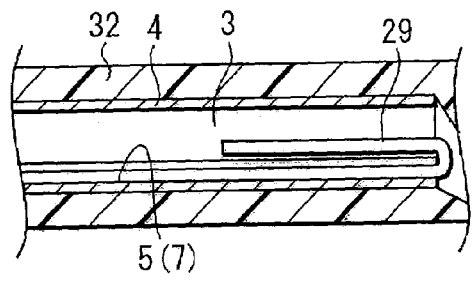
FIG. 6 is a sectional view taken along line 6—6 of FIG. 7.
Figure 7:
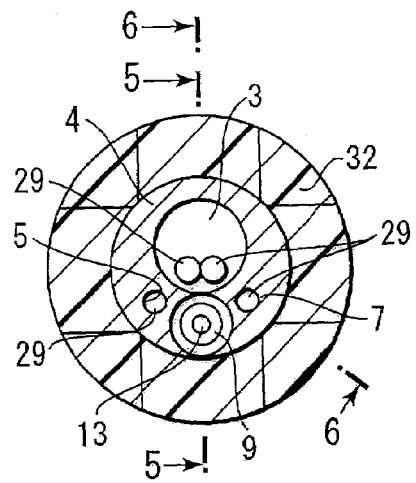
FIG. 7 is a sectional view taken along line 7—7 of FIG. 5.

The operating section 40 and the insert section 2 constructed in this manner can be connected by fixedly pressing the insert section 2 into a straight portion 31a of a tube body 31 that forms the connecting portion 40A. In this case, the reinforcing tube 24 of the insert section 2 extends close to the proximal end portion of the straight portion 31a of the tube body 31. Further, the tube 4 of the insert section 2 extends from the inside of the straight portion 31a of the tube body 31 into the connecting pipe portion 32 of the operator 40C through a second branch portion 31c, and terminates in the middle of the connecting pipe portion 32. In this case, the operating wire 13 that is passed through the fourth lumen 9 of the tube 4 extends beyond the proximal end of the tube 4 into the connecting pipe portion 32, and is connected to a slider 51 (see FIG. 8, mentioned later) of the operator body 70. Further, the stabilizers 29 that are passed through the second and third lumens 5 and 7 of the tube 4 are caused to project from the proximal end of the tube 4 and turned back toward the distal end side in the connecting pipe portion 32. Thereafter, the stabilizers 29 are inserted into the first lumen 3 and fixed in the first lumen 3 (FIGS. 6 and 7).

As shown in FIG. 5, a tube 39 extends from the distal end of the body 43 of the introducer 40B. The tube 39 extends through a first branch portion 31b of the tube body 31 of the connecting portion 40A, penetrates the side wall of the tube 4 of the insert section 2, and is pressed into the first lumen 3 of the tube 4. Further, a mouthpiece 44 to which a syringe for injecting the contrast medium or the like is connected is formed integrally on the flank of the body 43. In this case, the bore of the mouthpiece 44 communicates with the first lumen 3 of the insert section 2 by means of the respective bores of the body 43 and the tube 39. If the contrast medium is injected through the mouthpiece 44, therefore, the contrast medium can be guided into the first lumen 3 (and therefore, the contrast medium can be introduced into the living body through the end opening 3a of the first lumen 3).

Further, a guide wire inlet cylinder 45 is screwed into the basal part of the mouthpiece 44. In this case, a ring-shaped elastic member 49 is interposed between the inlet cylinder 45 and the mouthpiece 44, and the bore of the inlet cylinder 45 communicates with the bore of the mouthpiece 44 by means of the bore of the elastic member 49. If the inlet cylinder 45 is screwed into the mouthpiece 44, moreover, the elastic member 49 is crushed and elastically deformed so that the bore of the elastic member 49 is reduced in diameter. Accordingly, the guide wire that is inserted into the inlet cylinder 45 through an opening 45a of the inlet cylinder 45 is introduced into the first lumen 3 through the respective bores of the elastic member 49 and the body 43, and can project from the end opening 3a of the first lumen 3. If the inlet cylinder 45 is screwed into the body 43 to reduce the diameter of the elastic member 49 as this is done, moreover, no clearance is formed between the elastic member 49 and the guide wire that penetrates it. Thus, watertightness can be secured as the contrast medium is injected with use of the guide wire. In the case where the guide wire is not used, watertightness can be also secured by screwing the inlet cylinder 45 into the mouthpiece 44 in a like manner.

Figure 9:
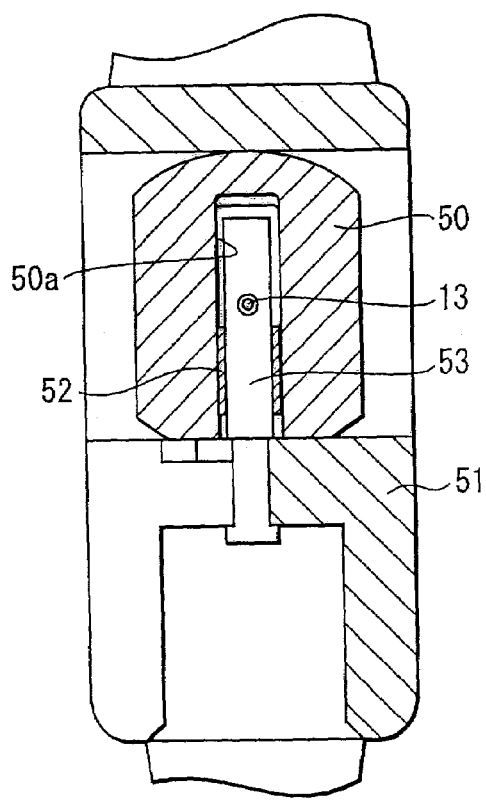
FIG. 9 is a sectional view taken along line 9—9 of FIG. 8.
Figure 10:
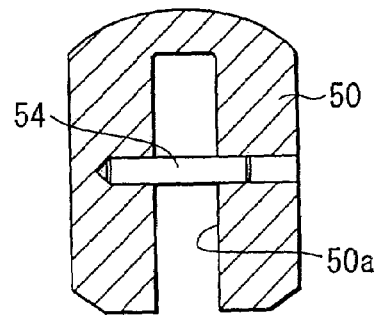
FIG. 10 is a sectional view taken along line 10—10 of FIG. 8.
Figure 8:
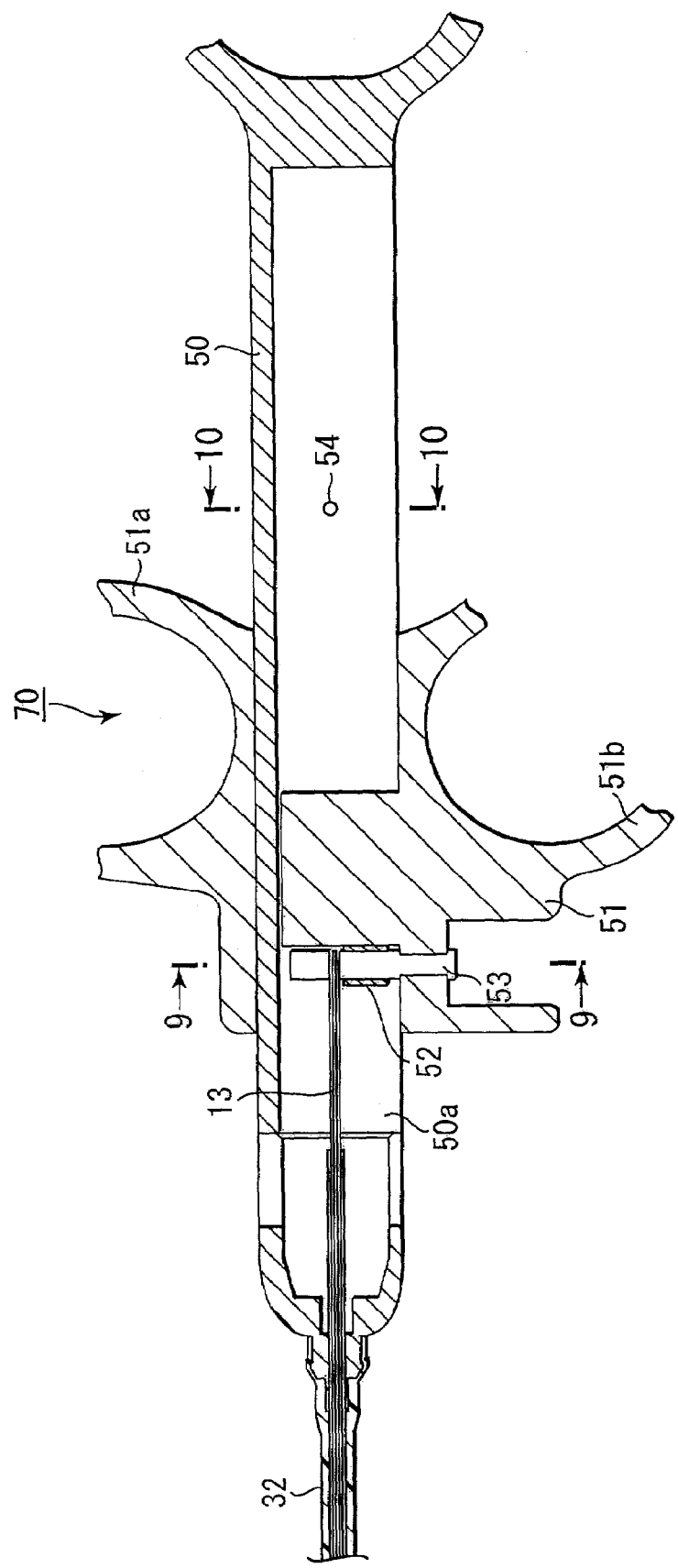
FIG. 8 is a sectional view of the body of an operator that constitutes the operating section.

FIGS. 8 to 10 show a detailed configuration of the operator body 70. As shown in FIG. 8, the operator body 70 is composed mainly of a body member 50 and the slider 51 that can advance and retreat in the longitudinal direction of the body member 50. The slider 51 is provided with two finger hooks 51a and 51b. Further, the slider 51 is fitted with a wire fixing pin 53 that projects into the body member 50. This wire fixing pin 53 is fixedly connected to the proximal end portion of the operating wire 13 that extends from the inside of the connecting pipe portion 32 into the body member 50.

As is evident from FIG. 9, a guide hole 50a for guiding the slider 51 in movement is formed extending in the longitudinal direction in the body member 50. Further, the wire fixing pin 53 that is integral with the slider 51 can also advance and retreat along the guide hole 50a. Furthermore, the outer peripheral surface of the wire fixing pin 53 is covered with a tube 52 that is in sliding contact with the inner surface of the guide hole 50a with a given coefficient of friction so that the wire fixing pin 53 can slide with the given coefficient of friction with respect to the body member 50, and more specifically, that the moved position of the wire fixing pin 53 (and therefore, of the slider 51) is maintained with the tube 4 bent, whereby the bent state of the tube 4 can be maintained.

In order to regulate the retreat of the slider 51 to restrict the curvature of the tube 4, moreover, the body member 50 is provided with a stopper pin 54 that extends across the guide hole 50a and can abut against the slider 51 (see FIG. 10).

If the slider 51 is manually advanced or retreated, according to this configuration, therefore, the operating wire 13 is pushed or pulled, and the distal end side of the tube 4 is bent in the UP or DOWN direction within a given range that is determined by means of the stopper pin 54. If the slider 51 is unhanded, the slider 51 is held as it is, and the bent state of the tube 4 can be maintained.

The following is a brief description of the way the catheter with the aforementioned configuration is endoscopically guided to, for example, a duodenal papilla.

Figure 12:
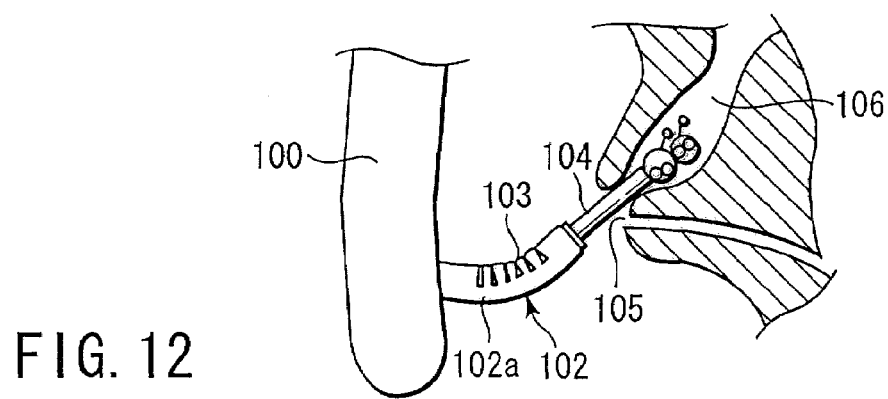
FIG. 12 is a view showing a conventional catheter made to approach a duodenal papilla.

As in the case shown in FIG. 12, the insert section of the endoscope is first inserted into a region near the duodenal papilla, and the insert section 2 of the catheter according to the present embodiment is then inserted into the channel of the insert section of the endoscope. In inserting the insert section 2 of the catheter into the channel of the endoscope, the insert section 2 is oriented (in the rotating direction) in advance so that the insert section 2 projects from the distal end of the insert section of the endoscope with the notches 10 directed toward the duodenal papilla. Thus, if the insert section 2 of the catheter of the present embodiment is previously oriented when it is inserted into the channel of the endoscope, there is no possibility of the insert section 2 being redirected by its own rotation or the like as the insert section 2 passes thereafter through the channel of the endoscope even though the insert section of the endoscope winds intricately in the living body. The reason is that the insert section 2 of the catheter of the present embodiment is provided with the two stabilizers 29 that define the one plane P parallel to the longitudinal central axis O of the insert section 2 (tube 4), and that the plane P determines the direction of the notches 10 when the insert section 2 is introduced into the channel of the endoscope. In consequence, therefore, the insert section 2 can be caused to project from the distal end of the endoscope with the side of the insert section 2 for the notches 10 directed toward the duodenal papilla.

After the distal end side of the insert section 2 of the catheter is thus caused to project from the insert section of the endoscope with the notches 10 directed toward the duodenal papilla, the distal end side of the projected insert section 12 is bent and directed toward the duodenal papilla. If the distal end side of the insert section 2 is bent by pulling the slider 51 of the operating section 40 to the hand side, the distal end of the insert section 2 can be directed successfully toward the duodenal papilla. In this case, the bending operation of the insert section 2 can also be stabilized in the rotation direction by means of the two stabilizers 29.

During this bending operation, moreover, there is no possibility of the tube 4 meandering owing to the flexibility of the elongate tube 4. This is because the reinforcing tube 24 that is formed of a heat-shrinkable tube is put on the outer peripheral surface of the tube 4, substantially covering the overall length of the insert section 2 except the distal end side on which the notches 10 are formed, according to the present embodiment. During the bending operation of the tube 4 by means of the operating wire 13, the reinforcing tube 24 prevents meandering of the tube 4 by restraining its compression, so that a handling force for the slider 51 on the hand side can be efficiently accurately transmitted to the distal end side. Thus, the distal end side of the insert section 2 can be bent to a desired degree, so that the distal end of the insert section 2 can be directed toward the duodenal papilla exactly and speedily.

During this bending operation, moreover, the stiffness of the distal end side of the tube 4 is lowered by the notches 10, so that the distal end side can be bent with ease. Accordingly, a desired curvature can be obtained with use of a small handling force, and the eccentric form of the notches 10 can somewhat regulate the bending direction of the insert section 2 (the side with the notches 10 is easily bendable).

In the catheter of the present embodiment, which is thus used in combination with the endoscope, the overall length of the tube 4 is about 500 mm greater than the length of the channel of the endoscope. In the case of the present embodiment, therefore, the bent portion of the tube 4 in which the notches 10 are formed must be formed extending for a range of 500 mm from the distal end of the tube 4 to the proximal end side.

In the catheter of the present embodiment, as described above, the notches 10 are provided on the distal end side of the tube 4, and further, the insert section 2 can be caused to project from the endoscope with the notches 10 directed toward the duodenal papilla by the agency of the stabilizers 29, and the handling force on the hand side can be efficiently accurately transmitted to the distal end side by means of the reinforcing tube 24 that cooperates with the stabilizers 29, without failing to maintain the direction of projection steadily. Thus, the distal end side of the insert section 2 can be bent to a desired degree in a desired direction, so that the distal end of the insert section 2 can be directed toward the duodenal papilla exactly and speedily.

If the slider 51 in the catheter of the present embodiment is unhanded, moreover, the slider 51 is held as it is, and the bent state of the tube 4 can be maintained, so that the slider 51 need not be held down to maintain the bent state. Thus, other treatments and operations, such as the manipulation of the guide wire, injection of the contrast medium, etc., can be concentrated on.

Although the present embodiment has been described for the case where the catheter is made to approach the duodenal papilla, it is to be understood that the catheter of the present embodiment can be caused to approach various regions of a living body as well as the duodenal papilla with the same functions and effects as aforesaid. Although the two stabilizers 29 are used in the present embodiment, moreover, three or more stabilizers may be used as long as they can define the one plane P.

According to the catheter of the present invention, as described above, the insert section can be caused to project in a desired direction from the distal end of the endoscope, and the direction of its projection can be maintained steadily.

Further, the handling force on the hand side can be efficiently and accurately transmitted to the distal end side, so that the distal end of the insert section can be directed toward a desired region of a living body exactly and speedily.

What is claimed is:

1. A catheter comprising:
   a flexible tubular insert section having a longitudinal central axis defining an imaginary plane including the longitudinal central axis, the flexible tubular insert section having a distal end portion including a distal end, a proximal end, and a lumen formed in the flexible tube and having an opening at the distal end, and the lumen extending to the distal end from the proximal end through the distal end portion for feeding liquid and/or an elongated member to the opening from the proximal end, and outwardly projecting the liquid and/or the elongated member from the opening, the distal end portion having a plurality of notches formed in an outer surface and arranged along the longitudinal central axis on one side of the imaginary plane, each of said plurality of notches not extending to the lumen so that each of said plurality of notches do not communicate with the lumen;
   an operating wire passed through said insert section and capable of advancing or retreating to bend the distal end portion of said insert section having said notches; and
   a reinforcing tube put on the insert section to cover at least a portion of the elongated portion except for said plurality of notches to restrain longitudinal compression of the portion of the insert section on which the reinforcing tube is put on.

2. A catheter according to claim 1, wherein at least two reinforcing wires extending along the longitudinal central axis and defining one plane substantially parallel to the imaginary plane are arranged in the insert section on said one side of said insert section in which said notches are formed.

3. A catheter according to claim 1, wherein said operating wire is not situated beyond an outside diameter of the insert section at least on the distal end portion of said insert section in which said notches are formed.

4. A catheter according to claim 1, wherein at least a part of said operating wire is formed of a single wire.

5. A catheter according to claim 1, wherein said insert section has a liquid feed passage extending along the longitudinal central axis, through which a liquid is passed.

6. A catheter according to claim 1, wherein said plurality of notches are formed only on said one side of the imaginary plane.

7. A catheter according to claim 1, wherein said reinforcing tube is provided outside of a portion of the elongated portion that is between the distal end of the insertion section and said plurality of notches.

8. A catheter according to claim 1, wherein said lumen has a central axis positioned on the other side of the imaginary plane where the notches are not formed.

9. A catheter according to claim 8, wherein said flexible tubular insert section has another lumen having a central axis positioned on said one side of the imaginary plane.

10. A catheter comprising:
    a flexible sheath capable of being inserted into a channel of an endoscope and passing a guide wire, the flexible sheath having, a distal end portion, a proximal end portion, and a lumen formed in the flexible sheath and having an opening at the distal end portion, the lumen extending to the distal end portion from the proximal end portion for feeding liquid and/or an elongated member to the opening from the proximal end portion, and outwardly projecting the liquid and/or the elongated member from the opening, the distal end portion having a plurality of notches formed in an outer surface and arranged along a longitudinal direction of the flexible sheath, each of said plurality of notches not extending to the lumen so that each of said plurality of notches do not communicate with the lumen;
    a reinforcing tube to cover a portion of the flexible sheath between the distal end portion and proximal end portion;
    an operating wire extending in the flexible sheath, fixed to the distal end portion of said flexible sheath at one end and not situated beyond an outside diameter of the flexible sheath at least on the distal end portion of said flexible sheath in which said plurality of notches are provided; and
    an operating section coupled to the proximal end portion of said flexible sheath and used to advance and retreat said operating wire in the longitudinal direction of said flexible sheath
    wherein the reinforcing tube reduces unintentional meandering of the flexible sheath.

11. A catheter according to claim 10, wherein at least a part of said operating wire is formed of a single wire.

12. A catheter according to claim 10, wherein said flexible sheath has a liquid feed passage extending in the longitudinal direction thereof, through which a liquid is passed.

13. A catheter according to claim 10, wherein said plurality of notches are located one-sidedly with eccentricity to a plane passing through a longitudinal axis of said flexible sheath.

14. A catheter according to claim 13, wherein at least two reinforcing wires extending in the longitudinal direction, defining one plane substantially parallel to the longitudinal axis of the flexible sheath are arranged in the flexible sheath on said one side of said flexible sheath on which said plurality of notches are formed.

15. A catheter according to claim 10, wherein said flexible sheath has a longitudinal central axis defining an imaginary plane including the longitudinal central axis, said plurality of notches are formed on one side of the imaginary plane, and said lumen has a central axis positioned on the other side of the imaginary plane, where the notches are not formed.

16. A catheter according to claim 15, wherein said flexible sheath has another lumen having a central axis positioned on said one side of the imaginary plane.

17. A catheter comprising:
    a flexible tubular insert section having, in an outer surface of a distal end side of the insert section, a plurality of notches arranged along a longitudinal axis of the insert section on one side of a first imaginary plane passing through the longitudinal axis of the insert section;
    an operating wire passed through said insert section and capable of advancing or retreating to bend the distal end side of said insert section having said notches; and
    at least two reinforcing wires extending along the longitudinal axis of the insert section and arranged in the insert section on said one side of the insert section in which the notches are formed and defining a second imaginary plane parallel to the longitudinal axis of the insert section.

18. A catheter according to claim 17, wherein the first and second imaginary planes are parallel to each other.

19. A catheter comprising:

a flexible tubular insert section having a longitudinal central axis defining an imaginary plane including the longitudinal central axis, the flexible tubular insert section having a distal end portion including a distal end, a proximal end, and a lumen formed in the flexible tube and having an opening at the distal end, the lumen extending to the distal end from the proximal end through the distal end portion for feeding liquid and/or an elongated member to the opening from the proximal end, and outwardly projecting the liquid and/or the elongated member from the opening, the distal end portion having a plurality of notches in an outer surface and arranged along the longitudinal central axis on one side of the imaginary plane, each of said plurality of notches not extending to the lumen so that each of said plurality of notches do not communicate with the lumen, and at least one stabilizer extending to the longitudinal central axis of the flexible tubular insert section and defining one plane substantially parallel to the imaginary plane including said stabilizer, wherein the stabilizer stabilizes passing and bending operations for the flexible tubular insert section in a rotating direction.

20. A catheter according to claim 19, wherein said at least one stabilizer includes at least two stabilizers inserted in the tubular insert section.

* * * * *